US009695095B2

(12) United States Patent
Dubreuil et al.

(10) Patent No.: US 9,695,095 B2
(45) Date of Patent: Jul. 4, 2017

(54) PROCESS FOR PREPARING A CATALYST BASED ON A GROUP VIII METAL AND CONTAINING SILICON, AND A PROCESS OF SELECTIVE HYDROGENATION IMPLEMENTING SAID CATALYST

(71) Applicant: IFP Energies nouvelles, Rueil-Malmaison (FR)

(72) Inventors: Anne-Claire Dubreuil, Lyons (FR); Filipe Manuel Marques Mota, Lyons (FR); Josselin Janvier, Nanterre (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 206 days.

(21) Appl. No.: 14/402,620

(22) PCT Filed: Apr. 5, 2013

(86) PCT No.: PCT/FR2013/050755
§ 371 (c)(1),
(2) Date: Nov. 20, 2014

(87) PCT Pub. No.: WO2013/175085
PCT Pub. Date: Nov. 28, 2013

(65) Prior Publication Data
US 2015/0141718 A1    May 21, 2015

(30) Foreign Application Priority Data
May 24, 2012   (FR) ..................................... 12 01492

(51) Int. Cl.
| | | |
|---|---|---|
| *C07C 5/05* | (2006.01) | |
| *B01J 37/16* | (2006.01) | |
| *B01J 37/20* | (2006.01) | |
| *B01J 23/44* | (2006.01) | |
| *B01J 23/755* | (2006.01) | |
| *B01J 37/02* | (2006.01) | |
| *C10G 45/36* | (2006.01) | |
| *C10G 45/40* | (2006.01) | |
| *C10G 69/06* | (2006.01) | |
| *C10G 9/36* | (2006.01) | |
| *B01J 31/26* | (2006.01) | |
| *B01J 37/18* | (2006.01) | |

(52) U.S. Cl.
CPC ................ *C07C 5/05* (2013.01); *B01J 23/44* (2013.01); *B01J 23/755* (2013.01); *B01J 31/26* (2013.01); *B01J 37/0201* (2013.01); *B01J 37/0203* (2013.01); *B01J 37/16* (2013.01); *B01J 37/18* (2013.01); *B01J 37/20* (2013.01); *C10G 9/36* (2013.01); *C10G 45/36* (2013.01); *C10G 45/40* (2013.01); *C10G 69/06* (2013.01); *B01J 2231/645* (2013.01); *B01J 2531/005* (2013.01)

(58) Field of Classification Search
CPC .. C07C 5/05; B01J 23/44; B01J 23/755; B01J 31/26; B01J 37/16; B01J 37/18; B01J 37/0201; B01J 37/0203; B01J 37/20; B01J 2231/645; B01J 2531/005; C10G 46/36; C10G 45/40
USPC ........................ 502/259, 262, 326, 337, 339
See application file for complete search history.

(56) References Cited

U.S. PATENT DOCUMENTS

| | | | | |
|---|---|---|---|---|
| 3,472,763 A | * | 10/1969 | Page ........................ | B01J 23/78 208/143 |
| 4,571,442 A | * | 2/1986 | Cosyns .................... | C07C 5/08 208/255 |
| 4,734,540 A | * | 3/1988 | Gattuso .................. | B01J 23/755 585/260 |
| 4,906,602 A | * | 3/1990 | Schneider ............ | B01J 23/8926 502/304 |
| 5,417,844 A | * | 5/1995 | Boitiaux ................ | B01J 23/755 208/143 |
| 7,645,376 B2 | * | 1/2010 | Bouchy ................... | B01J 23/85 208/108 |
| 8,067,334 B2 | * | 11/2011 | Hill ........................ | C10G 45/40 502/325 |
| 2009/0143491 A1 | | 6/2009 | Van Den Brink | |
| 2009/0318739 A1 | * | 12/2009 | Liu ..................... | B01J 23/8872 585/276 |

(Continued)

FOREIGN PATENT DOCUMENTS

| | | |
|---|---|---|
| DE | 19757990 A1 | 7/1998 |
| WO | 2012029714 A1 | 3/2012 |

OTHER PUBLICATIONS

International Search Report for PCT/FR2013/050755 dated Oct. 21, 2013.

(Continued)

*Primary Examiner* — Patricia L Hailey
(74) *Attorney, Agent, or Firm* — Millen White Zelano and Branigan, PC; Csaba Henter; John Sopp

(57) ABSTRACT

A process for preparing a selective hydrogenation catalyst is described, wherein is provided a catalyst precursor, comprising at least one group VIII metal in the metallic form, and at least one support formed of at least one oxide, characterized in that a step is performed of contacting the said catalyst precursor in the metallic form, in the liquid phase and in the presence of a reducing and/or inert atmosphere, with a non-polar solvent containing a silicon compound, the said silicon compound is selected from the silanes containing at least one Si—H bond and at least one Si—C bond, the silanols and the cyclic siloxanes.

The selective hydrogenation process implementing the said catalyst is also described.

11 Claims, No Drawings

(56) References Cited

U.S. PATENT DOCUMENTS

2011/0166398 A1* 7/2011 Fischer ............... B01J 23/835
585/263
2012/0071700 A1 3/2012 Huang et al.

OTHER PUBLICATIONS

Quintanilla, A. et al., "Tuning the support adsorption of Pd/SiO2 by silylation to improve the selective hydrogenation of aromatic ketones," Journal of Catalysis, 2008, vol. 257, pp. 55-63.
English Abstract of DE19757990, Publication Date: Jul. 2, 1998.
English Abstract of WO2012029714, Publication Date: Mar. 8, 2012.

* cited by examiner

PROCESS FOR PREPARING A CATALYST BASED ON A GROUP VIII METAL AND CONTAINING SILICON, AND A PROCESS OF SELECTIVE HYDROGENATION IMPLEMENTING SAID CATALYST

FIELD OF THE INVENTION

The field of the invention is that of selective hydrogenation processes. Selective hydrogenation processes allow the transformation of polyunsaturated compounds of oil cuts by converting the most highly unsaturated compounds to the corresponding alkenes while avoiding total saturation and therefore the formation of the corresponding alkanes. In the case of steam-cracking gasolines used as the feed, selective hydrogenation also enables alkenylaromatic compounds to be selectively hydrogenated to aromatic compounds.

The object of the invention is to propose a catalyst which performs better, notably in respect of activity and selectivity, when applied to the process of selective hydrogenation of the unsaturated hydrocarbon compounds present in hydrocarbon cuts, preferably cuts derived by steam cracking. The invention relates more particularly to a process for preparing the said catalyst, as well as to the hydrogenation process implementing the said catalyst.

PRIOR ART

Selective hydrogenation catalysts are generally based on metals in group VIII of the periodic table, preferably palladium or nickel. The metal is present in the form of metallic particles deposited on a support, which may be a refractory oxide in the form of beads, extrudates, or forms having other geometries. The metal content, the size of the particles of metal, and the distribution of the active phase in the support are among the criteria that are important for catalyst activity and selectivity.

These catalysts are used in selective hydrogenation processes by bringing a feed into contact with these catalysts, said feed generally being selected from the group consisting of C3, C4 or C5 steam-cracking cuts and steam-cracking gasolines, also termed pyrolysis gasolines. The aim of selective hydrogenation is to selectively hydrogenate the polyunsaturated compounds, notably the acetylene and diolefin compounds, to corresponding alkenes. In the case where steam-cracking gasolines are used as the feed, selective hydrogenation also allows the alkenylaromatic compounds to be selectively hydrogenated to aromatic compounds.

Like all catalysts, selective hydrogenation catalysts prove to be fragile under the influence of certain contaminants present in hydrocarbon cuts, notably the feeds derived by steam cracking.

One of the contaminants of steam-cracking feeds is silicon. Although present in the feeds in low concentrations, it poisons the catalysts used for selective hydrogenation of these feeds. In particular, with reference to Pd- or Ni-based catalysts used for selective hydrogenation of steam-cracking gasolines, silicon contents of 5000 ppm, or even 1.5 wt. %, can be recovered from "spent" catalysts discharged from industrial facilities.

Numerous pieces of research report the poisoning of catalysts by silicon. The paper *"Reactions of Organosilicon Compounds on Metals: III. Selective Poisoning by $Et_3SiH$ of Catalytic Hydrogenation and Dehydrogenation"* (A. Molnar, I. Bucsi, M. Bartok, F. Notheisz, and G. V. Smith, Journal of Catalysis 98, 386, (1986)) describes, for example, the effect of poisoning of group VIII metal-based catalysts with silicon, which is manifested as a reduced activity of these catalysts. The paper *"Modified Activities and Selectivities of Silated-oxidized-Reduced Pd and Pt catalysts"* (G. V. Smith, S. Tjandra, M. Musoiu, T. Wiltowski, F. Notheisz, M. Barták, I. Hannus, D. Ostgard, and V. Malhotra, Journal of Catalysis 161, 441 (1996)) describes the same phenomenon, and indicates that catalysts poisoned with silicon may be reactivated by an oxidation-reduction treatment. The silicon compound used is triethylsilane $Et_3SiH$ or silane $SiH_4$, introduced onto the catalyst discontinuously (in pulses) under a hydrogen, or inert atmosphere at high temperature (250° C.).

However, in certain cases the presence of silicon compounds in selective hydrogenation catalysts yields a beneficial effect of the reaction. Indeed, the paper entitled *"Properties of Si-modified Pd catalyst for selective hydrogenation of acetylene"* (E. W. Shin, C. H. Choi, K. S. Chang, Y. H. Na, and S. H. Moon, Catalysis Today 44, 137 (1998)) describes, in regard to the selective hydrogenation of acetylene into ethylene by a Pd-based supported catalyst, modified by addition of a silicon compound, an increase in ethylene selectivity. Silicon addition is achieved by chemical vapour deposition (CVD), by introducing quantities of $SiH_4$ discontinuously into a hydrogen atmosphere at 250° C., followed by oxidation. The paper *"Performance of Si-modified Pd catalyst in acetylene hydrogenation: catalyst deactivation behavior"* (W. J. Kim, E. W. Shin, J. H. Kang, S. H. Moon, Applied Catalysis A: General 251, 305 (2003)) describes the same reaction and discloses a reduction in the deactivation of the catalyst Pd in the presence of silicon. US patent 2006/0229478 describes a supported catalyst based on Pd and La, and modified with a silicon compound such as $SiH_4$, $SiHEt_3$, or phenylsilane, introduced by the CVD method. This catalyst shows improved ethylene selectivity in selective hydrogenation of acetylene to ethylene.

Also known are supported catalysts based on silicon-doped group VIII metals, which find an application in hydrotreatment reactions (described, for example, in patents WO95/11753 and EP955089). During the preparation of these catalysts, the silicon is introduced in the liquid phase by impregnation of a silicon compound either without solvent or in the presence of an aqueous and/or alcoholic solvent. In all cases, the catalysts thus silicated are subsequently subjected to a calcination step before being used in hydrotreatment. The calcination is conducted in an oxidising atmosphere between 150 and 600° C. They thus undergo oxidation.

Patent US2012/0071700 describes supported catalysts for the hydrogenation of unsaturated hydrocarbons comprising at least one active metallic component selected from palladium, platinum, nickel, copper, and ruthenium, and at least one silicon compound. The silicon compound may be introduced in the liquid phase or the gaseous phase. It is selected from the organic silanes, the organic siloxanes, the organic silazanes, and the organic chlorosilanes.

Surprisingly, the Applicant discovered that obtaining selective hydrogenation catalysts by a process of preparation with the aid of certain siliceous molecules and under certain conditions, notably in the liquid phase and in the presence of a non-polar solvent, enabled the activity of these catalysts in selective hydrogenation reactions to be greatly improved. The present invention thus describes a new type of catalyst which, on the strength of its specific method of preparation, will enable a catalyst to be obtained which, while being more active in selective hydrogenation, retains its elevated selectivities. Furthermore, for some silicon compounds, an increase in selectivity is simultaneously observed.

Contacting in the liquid phase and in the presence of a non-polar solvent has the advantage of being suitable for silica compounds of low volatility. In addition, better control is obtained of the quantity of silica compound deposited as compared with contact in the gaseous phase.

The present invention also relates to the catalyst obtainable by the preparation process according to the invention, as well as to a selective hydrogenation process implementing the catalyst prepared according to the invention.

DETAILED DESCRIPTION OF THE INVENTION

More particularly, the invention relates to a process for preparing a selective hydrogenation catalyst, wherein is provided a catalyst precursor comprising at least one group VIII metal in the metallic form and at least one support formed of at least one oxide, characterised in that a step is performed of contacting the said precursor, in the metallic form, in the liquid phase and in the presence of a reducing and/or inert atmosphere, with a non-polar solvent containing a silicon compound, and the said silicon compound is selected from the silanes containing at least one Si—H bond and at least one Si—C bond, the silanols and the cyclic siloxanes.

Thus catalyst thus prepared does not require a subsequent calcination step. Calcination is here understood as a heat treatment in an oxidising atmosphere at a temperature above 150° C.

The catalyst prepared according to the invention comprises an active metallic phase deposited on a support, the said active phase comprising at least one metal from group VIII of the periodic table of the elements, preferably selected from palladium and nickel. Very preferably, the said group VIII metal is palladium.

The said group VIII metal(s) is (are) in the form of metallic particles deposited on the said support. Generally, the content of group VIII metals in the catalyst is within the range 0.01 to 50 wt. % of the mass of the catalyst prepared according to the process of the invention, preferably 0.05 to 30 wt. % of the mass of the catalyst.

Preferably, when the active phase comprises palladium, the palladium content in the said catalyst prepared according to the process [of] the invention is advantageously within the range 0.01 to 5 wt. % of the mass of the catalyst, preferably 0.05 to 2 wt. % of the mass of the catalyst, and yet more preferably 0.05 to 1 wt. % of the mass of the catalyst.

Preferably, when the active phase comprises nickel, the nickel content in the said catalyst prepared according to the process [of] the invention is advantageously within the range 1 to 50 wt. % of the mass of the catalyst, more preferably 5% to 40 wt. % of the mass of the catalyst, and yet more preferably 5 to 30 wt. % of the mass of the catalyst.

The active phase of the said catalyst may further comprise at least one additional metal selected from the group VIII metals, the group IB metals and/or tin. The additional group VIII metal is preferably selected from platinum, ruthenium and rhodium, as well as palladium (in the case of a catalyst based on nickel) and nickel (in the case of a catalyst based on palladium). The additional group IB metal is advantageously selected from copper, gold and silver. The said additional group VIII and/or group IB metal(s) is (are) preferably present in a content representing 0.01 to 20 wt. % of the mass of the catalyst, preferably 0.05 to 10 wt. % of the mass of the catalyst and yet more preferably 0.05 to 5 wt. % of the mass of the said catalyst. The tin is preferentially present in a content representing 0.02 to 15 wt. % of the mass of the catalyst, so that the ratio Sn/group VIII metal(s) is within the range 0.01 to 0.2, preferably 0.025 to 0.055, and yet more preferably 0.03 to 0.05.

When the catalyst comprises palladium, it is preferable to deposit the palladium in a thin crust at the periphery of the support grains, as for example described in patent FR2922784. The palladium content in this catalyst is within the range 0.05 to 2 wt. % and at least 80 wt. % of the palladium is distributed in a crust at the periphery of the support. The thickness of this crust is generally within the range 10 to 1000 μm, preferably 20 to 600 μm, and yet more preferably 20 to 200 μm.

An especially preferable catalyst is described in patent FR2922784 and comprises palladium in a thin crust and in the metallic form, the said catalyst comprises at least one metal selected from the group consisting of the alkalis and the alkaline earths, a porous support comprising at least one refractory oxide selected from the group consisting of silica, alumina and silica-alumina, wherein the specific surface area of the porous support is within the range 50 to 210 m$^2$/g, the palladium content of the catalyst is within the range 0.05 to 2 wt. %, at least 80 wt. % of the palladium is distributed in a crust at the periphery of the support, the thickness of the said crust is within the range 20 to 200 μm, the metal dispersion D is within the range 25% to 70%, the density of palladium particles within the crust is within the range 1500 to 4100 palladium particles per μm$^2$, the sum of the contents of alkali and/or alkaline earth metals in the catalyst is within the range 0.05 to 5 wt. % and the said alkali and/or alkaline-earth metal is homogeneously distributed through the support with a coefficient R within the range 0.8 to 1.2, the said coefficient R being defined in FR2922784.

The support on which the said active phase is deposited is advantageously formed of at least one refractory oxide preferentially selected from the oxides of metals of groups IIA, IIIB, IVB, IIIA and IVA according to the CAS notation of the periodic table of the elements. The said support is preferably formed of at least one simple oxide selected from alumina ($Al_2O_3$), silica ($SiO_2$), titanium oxide ($TiO_2$), cerium oxide ($CeO_2$) and zirconium dioxide ($ZrO_2$). The said support is preferably selected from the aluminas, the silicas and the silica-aluminas. Highly preferably, the support is an alumina.

The pore volume of the support is generally within the range 0.1 cm$^3$/g to 1.5 cm$^3$/g, preferably 0.5 cm$^3$/g to 1.3 cm$^3$/g.

The specific surface area of the support is generally within the range 10 m$^2$/g to 250 m$^2$/g, preferably 30 m$^2$/g to 220 m$^2$/g.

The said porous support is advantageously in the form of beads, extrudates, pellets or irregular, non-spherical agglomerates, the specific form of which may be the result of a crushing step. Highly advantageously, the said support is in the form of beads or extrudates.

According to the invention, the step of introducing the silicon into the catalyst precursor is performed in the presence of a reducing and/or inert atmosphere and by placing the supported catalyst precursor comprising at least one group VIII metal in contact with a non-polar solvent containing a silicon compound, the said silicon compound is selected from the silanes containing at least one Si—H bond and at least one Si—C bond, the silanols and the cyclic siloxanes.

According to a first variant, the silicon compound may be selected from the silanes containing at least one Si—H bond and at least one Si—C bond. The silanes preferably correspond to the formula $Si_xH_yR_z$, wherein x is an integer within the range 1 to 6, y is an integer within the range 1 to 2x+1, and z is an integer within the range 1 to 2x+1, the sum of y+z being 2x+2. The R radical is a monovalent hydrocarbon radical, identical or different for each valence, and may be selected from a saturated aliphatic radical, an unsaturated aliphatic radical, a cycloalkyl radical, an aryl radical and an arylalkyl radical. The silanes preferably correspond to the formula $Si_xH_yR_z$, wherein x is an integer within the range 1 to 3, preferably x is equal to 1.

"Saturated aliphatic radical" is understood to mean, for R, a straight-chain or branched hydrocarbon chain having 1 to 15 carbon atoms, preferably 1 to 10 carbon atoms and yet more preferentially 1 to 4 carbon atoms. The saturated aliphatic radicals are preferably selected from the methyl, ethyl, propyl groups comprising n-propyl and isopropyl, butyl comprising n-butyl, isobutyl, sec-butyl and ter-butyl, and highly preferably from the methyl and ethyl groups.

"Unsaturated aliphatic radical" is understood to mean, for R, a straight-chain or branched hydrocarbon chain having 1 to 15 carbon atoms, preferably 1 to 10 carbon atoms and yet more preferentially 1 to 4 carbon atoms. Preferred unsaturated aliphatic radicals are advantageously selected from the vinyl, allyl, and methallyl groups.

"Cycloalkyl radical" is understood to mean, for R, a saturated cyclic hydrocarbon group preferably having 3 to 10 carbon atoms, notably a cyclopentyl or cyclohexyl group.

"Aryl radical" is understood to mean, for R, a preferably monocyclic or bicyclic aromatic group having 6 to 20 carbon atoms, and preferably phenyl or naphthyl.

"Arylalkyl radical" is understood to mean, for R, a straight-chain or branched hydrocarbon group bearing a monocyclic aromatic ring, having 7 to 12 carbon atoms, the aliphatic chain comprising 1 to 6 carbon atoms. A preferred arylalkyl group is the benzyl, tolyl, xylyl, ethylphenyl group.

More particularly, the silicon compound may be selected from trimethylsilane, triethylsilane, tripropylsilane, tributylsilane, methyldiethylsilane, methyldipropylsilane, methyldibutylsilane, dimethylethylsilane, dimethylpropylsilane, dimethylbutylsilane, ethyldipropylsilane, ethyldibutylsilane, diethylpropylsilane, diethylbutylsilane, propyldibutylsilane, dipropylbutylsilane, dimethylphenylsilane, dimethylcyclohexanesilane, diethylphenylsilane, methylethylphenylsilane, methyldiphenylsilane, ethyldiphenylsilane, methylsilane, ethylsilane, propylsilane, butylsilane, dimethylsilane, diethylsilane, dipropylsilane, dibutylsilane, methylethylsilane, methylpropylsilane, methylbutylsilane, ethylpropylsilane, ethylbutylsilane, propylbutylsilane, methyldisilane, dimethyldisilane, trimethyldisilane, tetramethyldisilane, pentamethyldisilane, ethyldisilane, diethyldisilane, triethyldisilane, tetraethyldisilane, pentaethyldisilane, propyldisilane, dipropyldisilane, tripropyldisilane, tetrapropyldisilane, pentapropyldisilane, butyldisilane, dibutyldisilane, tributyldisilane, tetrabutyldisilane, pentabutyldisilane, methyltrisilane, dimethyltrisilane, trimethyltrisilane, tetramethyltrisilane, pentamethyltrisilane, hexamethyltrisilane, heptamethyltrisilane, ethyltrisilane, diethyltrisilane, triethyltrisilane, tetraethyltrisilane, pentaethyltrisilane, hexaethyltrisilane, or heptaethyltrisilane. Triethylsilane is especially preferable.

According to another variant, the silicon compound may be selected from the silanols. Silanols is understood to mean compounds containing at least one silicon atom directly bound to a hydroxyl group. The silanols preferably comprise only one hydroxyl group and correspond to the formula $Si_x(OH)R_{2x+1}$, wherein x is an integer within the range 1 to 6, and R is a radical as defined above. The silanes correspond to the formula $Si_x(OH)R_{2x+1}$, wherein x is an integer within the range 1 to 3, preferably x is equal to 1. R is preferably a group selected from the methyl, ethyl, propyl groups comprising n-propyl and isopropyl, butyl group comprising n-butyl, isobutyl, sec-butyl and ter-butyl, and very highly preferably from the methyl and ethyl groups.

More particularly, the silicon compound may be selected from trimethylsilanol, triethylsilanol, tripropylsilanol, tributylsilanol, methyldiethylsilanol, methyldipropylsilanol, methyldibutylsilanol, dimethylethylsilanol, dimethylpropylsilanol, dimethylbutylsilanol, ethyldipropylsilanol, ethyldibutylsilanol, diethylpropylsilanol, diethylbutylsilanol, propyldibutylsilanol, dipropylbutylsilanol, dimethylphenylsilanol, dimethylcyclohexanesilanol, diethylphenylsilanol, methylethylphenylsilanol, methyldiphenylsilanol, and ethyldiphenylsilanol. Triethylsilanol is especially preferable.

According to another variant, the silicon compound may be selected from the cyclic siloxanes. By cyclic siloxanes is meant a siloxane in which the principal —Si—O—Si—O— chain forms a ring and is composed of $(R_2SiO)_n$ units, with n being an integer within the range 3 to 11, preferably 3 to 8, and R a radical as defined above. Preferably, R is a methyl group.

More particularly, the silicon compound may be selected from hexamethylcyclotrisiloxane, octamethylcyclotetrasiloxane, decamethylcyclopentasiloxane, dodecamethylcyclohexasiloxane, tetradecamethylcycloheptasiloxane and hexadecamethylcyclooctasiloxane.

Octamethylcyclotetrasiloxane is especially preferable.

The non-polar solvent is preferentially selected from a hydrocarbon solvent, for example an aliphatic hydrocarbon solvent such as hexane, heptane, octane, nonane, decane, a cyclic hydrocarbon solvent such as cyclohexane, an aromatic hydrocarbon solvent such as benzene, toluene or xylene, a partially saturated gasoline, a partially hydrogenated effluent derived from a subsequently performed selective hydrogenation process, or a mixture thereof. Heptane, a partially saturated gasoline, or the partially hydrogenated effluent derived from the selective hydrogenation process performed subsequently.

The silicon compound is preferably present in the non-polar solvent in a concentration between 0.01 and 10 wt. % of silicon, preferably 0.1 and 10 wt. % of silicon, preferably between 0.5 and 8 wt. % of silicon, and yet more preferably between 1 and 5 wt. % of silicon.

Preferentially, the contacting step is performed at a temperature within the range 20 to 200° C., preferably 20° C. to 180° C., and yet more preferably between 50 and 180° C. The pressure is generally between atmospheric pressure and the pressure at which the selective hydrogenation process will be conducted, that is, within the range 0.3 to 6.5 MPa.

The contact time of the supported catalyst precursor with the polar solvent containing the silicon compound is advantageously greater than 15 minutes, preferably greater than 1 hour, if the reaction is performed in a discontinuous (batch) system; in general it is 5 hours. In the case of use in a stationary reactor under continuous system conditions, the hourly space velocity (HSV) being defined as volume of feed/volume of catalyst/hour, is advantageously within the range 0.1 to 10 $h^{-1}$, preferably 0.2 to 5 $h^{-1}$, and yet more preferably 1 to 5 $h^{-1}$.

The catalyst precursor is placed in contact with the polar solvent containing the silicon compound in the presence of a reducing atmosphere (for example in the presence of hydrogen, pure or diluted) and/or in the presence of an inert atmosphere (for example in the presence of nitrogen).

The catalysts thus prepared necessitate no subsequent calcination step. Here, calcination is understood to mean a heat treatment in an oxidising atmosphere to a temperature above 150° C.

The catalyst obtained at the end of the preparation process of the invention is advantageously used directly at the end of the said silicon-introducing step in a reaction unit performing the conversion of a hydrocarbon feed, in particular in a reaction unit performing the selective hydrogenation of a feed of polyunsaturated hydrocarbons. The said catalyst prepared according to the method of the invention may also be stored in air then reduced prior to use. The reduction is then performed in a stream of reducing gas, preferably pure or diluted hydrogen, at high temperature, preferably above or equal to 2 hours.

The silicon introduction process according to the invention is conducted on a supported catalyst precursor present in the metallic (or reduced) form. By metallic form it is understood that the metals present on the support are at least partially, and preferably for the most part, in a zero degree of oxidation.

The silicon introduction step may be preceded by conventional steps of preparing selective hydrogenation catalysts that are known to the person skilled in the art.

Thus, according to a preferred variant, the process of preparing the catalyst further comprises the following steps, the said steps being performed prior to the contacting step:
  a) at least one step in which a solution containing at least one precursor of the said group VIII metal is impregnated onto the said support,
  b) at least one step in which the impregnated support resulting from step a) is dried,
  c) at least one step in which the dried support resulting from step b) is calcined, so as to obtain at least the said metal from the said group VIII in oxide form,
  d) at least one step in which a reductive treatment of the calcined support resulting from step c) is performed by contact with a reducing gas so as to obtain at least the said metal of the said group VIII in the metallic form.

The preparation process may further comprise a step e) in which a passivation of the catalyst precursor is performed with a sulphur compound. This passivation may be performed either after calcination step c) and before step d) of reductive treatment of the catalyst precursor, or after step d) of reductive treatment of the catalyst precursor, or even after the silicon-introduction step.

The different steps a), b), c), d), and e) for preparing the supported catalyst precursor in the metallic form are described below.

Impregnation Step

Impregnation step a) may be performed by all the methods familiar to the person skilled in the art. In particular, step a) may be performed by impregnation to excess or by dry impregnation. The impregnation may be performed in a single impregnation, or as a plurality of successive impregnations.

The said step a) is preferably performed by dry impregnation, which consists in placing the support in contact with the aqueous or organic solution (such as an alcoholic solvent) with a volume equal to the pore volume of the support to be impregnated.

When it is introduced in organic solution, the said group VIII metal precursor is, for example, the oxalate or acetate of the said group VIII metal. The said group VIII metal precursor is preferably introduced in aqueous solution, for example in the form of nitrate, carbonate, acetate, chloride, oxalate, hydroxide or of any other inorganic derivative that is soluble in aqueous solution.

In the case in which the said group VIII metal is palladium, the palladium precursor used in the aqueous phase is advantageously a precursor selected from palladium nitrate, palladium chloride, palladium sulphate, preferably palladium nitrate.

In the case in which the said group VIII metal is nickel, the nickel precursor used in the aqueous phase is advantageously a precursor selected from nickel nitrate, nickel chloride, nickel carbonate, nickel acetate and nickel hydroxide, preferably nickel nitrate.

When a palladium-based catalyst in a crust is to be obtained, one uses, for example, the colloidal impregnation method such as that described in FR2922784 and according to which a colloidal suspension of palladium oxide or palladium hydroxide in the aqueous phase is prepared by mixing an aqueous solution 1 comprising at least one hydroxide selected from the group consisting of the alkali hydroxides, preferably sodium hydroxide, and the alkaline earth hydroxides, with an aqueous solution 2 comprising at least one palladium salt precursor, the solution 2 then the solution 1 being poured into an apparatus or solutions 1 and 2 being poured simultaneously into an apparatus, the said colloidal suspension then being used to impregnate the support.

Drying Step

Step b) of drying of the impregnated support resulting from step a) is preferentially performed according to the preparation process of the invention, at a temperature within the range 20 to 160° C., preferably 20 to 130° C. Drying step b) is preferentially performed during a period within the range 1 to 24 hours, preferably 1 to 20 hours. The drying is performed in air or in an inert atmosphere (nitrogen, for example).

Calcination Step

At the end of drying step b), a step c) of calcination of the support is performed at a temperature within the range 150 to 800° C., preferably 250 to 600° C. and highly preferably 300 to 600° C. Generally, the calcination is performed in air. It is preferentially during a period within the range 1 to 6 hours. The catalyst precursor obtained at the end of the said step c) is in the oxide state.

Reduction Step

Prior to introduction of the silicon into the catalyst precursor and its subsequent use in the catalytic reactor and the implementation of the selective hydrogenation process, the catalyst precursor is subjected at least to a reductive treatment step d), by contact with a reducing gas, for example with pure or dilute hydrogen, at high temperature, typically above or equal to 50° C. for a period greater than or equal to 2 hours. This treatment enables the said precursor to be activated and to form particles of metal, in particular of group VIII metal, in the zero valence state. The said reductive treatment may be performed in-situ or ex-situ, that is, before the catalyst is fed into the selective hydrogenation catalyst. The said reductive treatment step d) may be implemented on the catalyst precursor that has or has not undergone the passivation step e).

Passivation Step

The preparation process according to the invention may comprise a step e) of passivation of the catalyst precursor with a sulphur compound, which step e) may be carried out either after calcination step c) and before step d) of reductive treatment of the catalyst precursor, or after step d) of reductive treatment of the catalyst precursor, or after the contacting step. The sulphur passivation step enables the selectivity of the catalysts to be improved.

When passivation step e) is performed after calcination step c) and before step d) of reductive treatment of the catalyst precursor, step e) is preferably carried out ex-situ, that is to say, prior to feeding of the catalyst into the selective hydrogenation reaction unit. The said step e) is performed by implementing methods known to the person skilled in the art and especially, by way of example, by implementing one of the methods described in the patents EPO466567, U.S. Pat. No. 5,153,163, FR2676184, WO2004/098774, or in EP0707890. The said step e) is preferably performed by placing the catalyst precursor obtained at the end of implementing step c) in contact with at least one solution comprising at least one organic reducing agent and at least one sulphur compound. The said step e) is highly preferably performed by impregnating the catalyst precursor obtained at the end of implementing step c) with the said solution. The organic reducing agent present in the said solution is selected, for example, from formic acid, ethanol, methanol, ethyl formate and methyl formate. The sulphur compound present in the said solution is, for example, a compound of the formula HO—R1-S—S—R2-OH (where R1 and R2 may be any type of organic radical) such as diethanol disulphide (DEODS), or a polysulphide organic compound of the formula R—S(n)-R', where R and R' are organic radicals and n is within the range 3 to 20, for example dodecyl polysulphide. The quantity of sulphur introduced is such that the catalyst passivated by the sulphur comprises 0.2 to 2 wt. % sulphur. The quantity of organic reducing agent introduced is such that the passivated catalyst comprises between 100 ppm (parts per million) and 50 wt. % of the said reducing agent. Following introduction of the said sulphur compound onto the catalyst, the said catalyst precursor is then subjected to a heat treatment performed at a temperature within the range 100 to 200° C. for a duration within the range 30 minutes to 3 hours. When passivation step e) is performed after step d) of reducing treatment of the catalyst precursor, or after the silicon introduction step, step e) is preferably performed in-situ, that is, within the same reactor as the one in which the selective hydrogenation reaction is performed. The said passivation step is carried out by injection of at least one sulphur compound before or after the contacting of the said catalyst precursor with the non-polar solvent containing the silicon compound. The sulphur compound is selected, for example, from the following compounds: thiophene, thiophane, alkylmonosulphides such as dimethyl sulphide, diethyl sulphide, dipropyl sulphide and propylmethyl sulphide.

Selective Hydrogenation Process

The present invention also relates to a process of selective hydrogenation of a polyunsaturated hydrocarbon feed containing at least 3 carbon atoms per molecule and having a final boiling point below or equal to 250° C., by placing the said feed in contact with at least the catalyst prepared in accordance with the preparation process of the invention.

The polyunsaturated hydrocarbon feed treated in the selective hydrogenation process is preferentially selected from the group C3 steam-cracking cut, C4 steam-cracking cut, C5 steam-cracking cut, and steam-cracking gasolines also known as pyrolysis gasolines. All these cuts and these steam-cracking gasolines containing at least 3 carbon atoms per molecule and have a final boiling point below or equal to 250° C. More precisely, the said polyunsaturated hydrocarbons present in the said treated feed are in particular compounds comprising at least one acetylenic function (that is, at least one triple bond) and/or at least one dienic function (that is, at least two double bonds). In particular, the said polyunsaturated hydrocarbon feed may comprise at least one type of compound containing both an acetylenic function and a dienic function per molecule. The pyrolysis gasoline feed may additionally contain alkenylaromatic compounds.

The processes for converting hydrocarbons, such as the steam cracking process, the preferential source of the said hydrocarbon feed to be treated according to selective hydrogenation process using the catalyst prepared according to the invention, are operated at high temperature and produce a great variety of monounsaturated molecules such as propylene, the straight-chain butenes, Isobutene, and the pentenes, as well as the monounsaturated molecules containing up to 15 carbon atoms. Polyunsaturated compounds having a plurality of double bonds and/or at least one triple bond are also formed in parallel, in particular acetylene, propadiene and methylacetylene (or propyne), 1,2-butadiene and 1,3-butadiene, butyne, vinylacetylene ethylacetylene, pentadiene, as well as other polyunsaturated compounds present in steam-cracking gasolines, in particular styrene and indene compounds.

All these polyunsaturated compounds must be eliminated to enable the use of these different cuts in petrochemical processes such as polymerisation or in refining processes.

The C3 steam-cracking cut, advantageously used for implementation of the selective hydrogenation process according to the invention, has, for example, the following mean composition: of the order of 90 wt. % propylene, of the order of 3 to 8 wt. % propadiene and methylacetylene, the residue being substantially propane. In certain C3 cuts, between 0.1 and 2 wt. % of C2 compounds and C4 compounds may also be present.

The C4 steam-cracking cut, advantageously used for implementation of the selective hydrogenation process according to the invention, has, for example, the following mean composition: 1 wt. % butane, 46.5 wt. % butene, 51 wt. % butadiene, 1.3 wt. % vinylacetylene (VAC) and 0.2 wt. % butyne. In certain C4 cuts, between 0.1 and 2 wt. % of C3 compounds and C5 compounds may also be present.

The C5 steam-cracking cut, advantageously used for implementation of the selective hydrogenation process according to the invention, has, for example, the following mean composition: 21 wt. % pentanes, 45 wt. % pentenes, 34 wt. % pentadienes.

The steam-cracking gasoline or pyrolysis gasoline, advantageously used for implementation of the selective hydrogenation process according to the invention, corresponds to a hydrocarbon cut the boiling point of which is generally within the range 0° C. to 250° C., preferably 10° C. to 220° C. The polyunsaturated hydrocarbons present in the said steam-cracking gasoline are, in particular, diolefin compounds (butadiene, isoprene, cyclopentadiene, etc.), styrene compounds (styrene, alpha-methylstyrene, etc.) and indene compounds (indene, etc.). The steam-cracking gasoline generally comprises the C5-C12 cut with traces of C3, C4, C13, C14, and C15 (for example between 0.1 and 3 wt. % for each of these cuts). For example, the steam-cracking gasoline may advantageously present the following distribution, depending on the chemical functions present in the compounds of the hydrocarbon feed (en wt. %):

Paraffins+naphthenes: 10-25
Aromatic compounds: 50-70
Monoolefins: 5-20
Diolefins: 10-25
Alkenylaromatic compounds: 2-10
Sulphur 5-500 ppm.

The selective hydrogenation process according to the invention aims to eliminate the said polyunsaturated hydrocarbons present in the said feed to be hydrogenated by converting the said polyunsaturated hydrocarbons to the corresponding alkenes while avoiding total saturation of the said hydrocarbons so as to avoid the formation of the corresponding alkanes.

For example, when the said feed is a C3 cut, the selective hydrogenation process according to the invention aims to selectively hydrogenate propadiene and methylacetylene. In the case of a C4 cut, the aim is to eliminate butadiene, vinylacetylene (VAC) and butyne, In the case of a C5 cut, the aim is to eliminate the pentadienes. When the said feed is a steam-cracking gasoline, the selective hydrogenation process according to the invention aims to selectively hydrogenate the said polyunsaturated hydrocarbons present in the said feed to be treated in such a way that the diolefin compounds are partially hydrogenated to mono-olefins and that the styrene and indene compounds are partially hydrogenated to corresponding aromatic compounds.

The technological implementation of the selective hydrogenation process according to the invention is achieved, for example, by injecting the polyunsaturated hydrocarbon feed and the hydrogen, in an ascending or descending current, into at least one fixed-bed reactor. The said reactor may be of the isothermal or adiabatic type. An adiabatic reactor is preferred. The polyunsaturated hydrocarbon feed may advantageously be diluted by one or more re-injection(s), at various points on the reactor located between the reactor inlet and outlet, of the effluent derived from the said reactor in which the selective hydrogenation reaction takes place. The technological implementation of the selective hydrogenation process according to the invention may also be advantageously achieved by implantation of at least the said catalyst prepared according to the process of the invention, which catalyst is supported in a reactive distillation column or in reactor-exchangers. The hydrogen flux may be introduced at the same time as the feed to be hydrogenated and/or at a different point on the reactor.

In the case of the feed being a C3 steam-cracking cut, a C4 steam-cracking cut, a C5 steam-cracking, or a steam-cracking gasoline, the selective hydrogenation process according to the invention is implemented in the liquid phase under the following operating conditions: a total pressure within the range 0.3 MPa to 6.5 MPa, more preferentially within the range 1 to 5 MPa, a temperature within the range 20 to 250° C. and a hydrogen/(polyunsaturated hydrocarbons to be hydrogenated) molar ratio within the range 0.1 to 4, preferably 1 to 2. The hourly space velocity (defined as the ratio of the volumetric flow rate to the volume of catalyst per hour) established under these conditions is generally within the range 0.2 to 100 $h^{-1}$. In the case of a steam-cracking gasoline, the hourly space velocity is generally within the range 0.5 to 20 $h^{-1}$, preferably 1 to 10 $h^{-1}$ and yet more preferably 2 to 10 $h^{-1}$.

The invention is illustrated by the examples which follow without, however, being limited in its scope thereby. These examples show, for the catalysts prepared according to the invention, an increase in activity in a selective hydrogenation reaction and, for some thereof, an increase in selectivity.

Example 1 (Comparison): Preparation of a Reference Catalyst A

A commercially available Pd/alumina catalyst (LD265, Axens) is used as the reference catalyst. The said commercial catalyst has a palladium content equal to 0.3 wt. %, a specific surface area equal to 70 $m^2/g$, and a total pore volume equal to 0.6 $cm^3/g$ for a bead diameter within the range 2 to 4 mm.

The said commercial catalyst is crushed and screened so as to retain only the granule sizes within the range 200 to 355 micrometers. A quantity of 1 g of this commercial catalyst is treated in a stream of hydrogen with a hydrogen flow rate of 1 NL/h, at 150° C. for 2 hours, with a temperature ramp-up of 300° C./h. The reduced sample thus obtained is denoted catalyst A. It is introduced directly into the autoclave with a view to the hydrogenation test described in example 12, in 140 mL of heptane, in the total absence of contact with the air.

Example 2 (According to the Invention): Preparation of a Catalyst B by Contacting with a Solution of Triethylsilane in Heptane Catalyst A in the metallic form, described in example 1, is introduced into the autoclave used for the hydrogenation test in 140 mL of heptane and in the total absence of contact with air. A quantity of 5.7 mL triethylsilane ($SiH(C_2H_5)_3$, CAS n° 617-86-7) is introduced into the heptane so as to obtain an Si concentration equal to approximately 1 wt. %. The autoclave is then sealed, purged and then pressurised under 10 bar (1 MPa) of hydrogen, and brought to a temperature of 50° C. This temperature is maintained for 5 hours, with agitation (1600 turns/min). The catalyst thus obtained is denoted catalyst B. It is used directly in the hydrogenation test described in example 12.

Example 3 (According to the Invention): Preparation of a Catalyst C by Contacting with a Solution of Triethylsilane in Heptane This preparation is identical to the one described in example 2 with the exception of the triethylsilane concentration. A quantity of 17.4 mL triethylsilane is introduced into the heptane, so as to obtain an Si concentration equal to approximately 3 wt. %. The catalyst thus obtained is denoted catalyst C. It is used directly in the hydrogenation test described in example 12.

Example 4 (According to the Invention): Preparation of a Catalyst D by Contacting with a Solution of Triethylsilanol in Heptane Catalyst A in the metallic form, described in example 1, is introduced into the autoclave used for the hydrogenation test in 140 mL of heptane and in the total absence of contact with air A quantity of 5.3 mL of triethylsilanol ($SiOH(C_2H_5)_3$, CAS n° 597-52-4) is introduced into the heptane so as to obtain an Si concentration equal to approximately 1 wt. %. The autoclave is then sealed, purged and then pressurised under 10 bar (1 MPa) of hydrogen, and brought to a temperature of 50° C. This temperature is maintained for 5 hours, with agitation (1600 turns/min). The catalyst thus obtained is denoted catalyst D. It is used directly in the hydrogenation test described in example 12.

Example 5 (According to the Invention): Preparation of a Catalyst E by Contacting with a Solution of Triethylsilanol in Heptane This preparation is identical to the one described in example 4 with the exception of the triethylsilanol concentration. A quantity of 16.6 mL triethylsilanol is introduced into the heptane, so as to obtain an Si concentration equal to approximately 3 wt. %. The catalyst thus obtained is denoted catalyst E. It is used directly in the hydrogenation test described in example 12.

Example 6 (According to the Invention): Preparation of a Catalyst F by Contacting with a Solution of Triethylsilanol in Heptane This preparation is identical to the one described in example 4 with the exception of the triethylsilanol concentration. A quantity of 28.3 mL triethylsilanol is introduced into the heptane, so as to obtain an Si concentration equal to approximately 5 wt. %. The catalyst thus obtained is denoted catalyst F. It is used directly in the hydrogenation test described in example 12.

Example 7 (According to the Invention): Preparation of a Catalyst G by Contacting with a Solution of Octamethylcyclotetrasiloxane in Heptane Catalyst A in the metallic form, described in example 1, is introduced into the autoclave used for the hydrogenation test in 140 mL of heptane and in the total absence of contact with air. A quantity of 2.7 mL octamethylcyclotetrasiloxane ($C_8H_{24}O_4Si_4$, CAS n° 556-67-2) is introduced into the heptane so as to obtain an Si concentration equal to approximately 1 wt. %. The autoclave is then sealed, purged and then pressurised under 10 bar (1 MPa) of hydrogen, and brought to a temperature of 50° C. This temperature is maintained for 5 hours, with agitation (1600 turns/min). The catalyst thus obtained is denoted catalyst G. It is used directly in the hydrogenation test described in example 12.

Example 8 (According to the Invention): Preparation of a Catalyst H by Contacting with a Solution of Octamethylcyclotetrasiloxane in Heptane This preparation is identical to the one described in example 7 with the exception of the operating conditions of contacting with the solution of octamethylcyclotetrasiloxane in heptane. The autoclave is pressurised under 10 bar (1 MPa) of hydrogen, and brought to the temperature of 70° C. This temperature is maintained for 7 hours, with agitation (1000 turns/min). The catalyst thus obtained is denoted catalyst H. It is used directly in the hydrogenation test described in example 12.

Example 9 (According to the Invention): Preparation of a Catalyst I by Contacting with a Solution of Octamethylcyclotetrasiloxane in Heptane This preparation is identical to the one described in example 7 with the exception of the operating conditions of contacting with the solution of octamethylcyclotetrasiloxane in heptane. The autoclave is pressurised under 30 bar (3 MPa) of hydrogen, and brought to the temperature of 180° C. This temperature is maintained for 17 hours, with agitation (1000 turns/min). The catalyst thus obtained is denoted catalyst I. It is used directly in the hydrogenation test described in example 12.

Example 10 (Comparison): Preparation of a Catalyst J by Contacting with a Solution of Dimethoxydimethylsiloxane in Heptane Catalyst A in the metallic form, described in example 1, is introduced into the autoclave used for the hydrogenation test in 140 mL of heptane and in the total absence of contact with air. A quantity of 4.7 mL dimethoxydimethylsiloxane ($Si(CH_3)_2(OCH_3)_2$, CAS n° 1112-39-6) is introduced into the heptane so as to obtain an Si concentration equal to approximately 1 wt. %. The autoclave is then sealed, purged and then pressurised under 10 bar (1 MPa) of hydrogen, and brought to a temperature of 50° C. This temperature is maintained for 5 hours, with agitation (1600 turns/min). The catalyst thus obtained is denoted catalyst J. It is used directly in the hydrogenation test described in example 12.

Example 11 (Comparison): Preparation of a Catalyst K by Contacting with a Solution of Hexamethyldisilane in Heptane Catalyst A in the metallic form, described in example 1, is introduced into the autoclave used for the hydrogenation test in 140 mL of heptane and in the total absence of contact with air. A quantity of 0.8 mL hexamethyldisilane ($Si_2(CH_3)_6$, CAS n° 1450-14-2) is introduced into the heptane so as to obtain an Si concentration equal to approximately 0.2 wt. %. The autoclave is then sealed, purged and then pressurised under 10 bar (1 MPa) of hydrogen, and brought to a temperature of 50° C. This temperature is maintained for 5 hours, with agitation (1600 turns/min). The catalyst thus obtained is denoted catalyst K. It is used directly in the hydrogenation test described in example 12.

Example 12 (According to the Invention): Catalytic Test of Hydrogenation of 1,3-Butadiene The catalytic properties of the catalysts prepared according to the above examples are evaluated in succession in a process of 1,3-butadiene hydrogenation. The selective hydrogenation of 1,3-butadiene leads to a mixture of the three isomers of butene (1-butene, cis-2-butene and trans-2-butene), this hydrogenation constituting the desired reaction. The total hydrogenation 1,3-butadiene leads to butane, which is produced by an undesirable adverse reaction.

The hydrogenation 1,3-butadiene is performed in a perfectly agitated "Grignard" reactor composed of a 250-mL stainless-steel autoclave, fitted with a mechanical agitator. hydrogenation is performed in the liquid phase, under a constant pressure of 10 bar (1 MPa) of hydrogen, at a temperature of 17° C. and under agitation at 1600 turns/min. The solvent is heptane (140 mL) and the feed is composed of 7 g 1,3-butadiene. The consumption of hydrogen is followed in the course of time by a loss of pressure in a bottle reservoir positioned upstream of the reactor. The reaction products are analysed by gas chromatography.

The catalytic activity is expressed in moles of $H_2$ consumed per second and per mole of Pd. The residual activity is defined as the ratio of the activity of the catalyst prepared by contact with a solution containing a silicon compound to the activity of the reference catalyst. A residual activity above 100 indicates that the test catalyst is more active than the reference catalyst. Conversely, a residual activity below 100 indicates that the test catalyst is less active that the reference catalyst. The residual activities of the catalysts prepared according to the examples above are given in Table 1.

TABLE 1

Residual activities of the catalysts prepared according to the examples above

| Catalyst | Silicon compound used | Residual activity (%) |
|---|---|---|
| A (reference) | — | 100 |
| B | triethylsilane - 1 wt. % Si | 128 |
| C | triethylsilane - 3 wt. % Si | 222 |
| D | triethylsilanol - 1 wt. % Si | 126 |
| E | triethylsilanol - 3 wt. % Si | 186 |
| F | triethylsilanol - 5 wt. % Si | 144 |
| G | octamethylcyclotetrasiloxane - 50° C. | 149 |
| H | octamethylcyclotetrasiloxane - 70° C. | 248 |
| I | octamethylcyclotetrasiloxane - 180° C. | 176 |
| J | dimethoxydimethylsiloxane | 71 |
| K | hexamethyldisilane | 97 |

Catalysts B and C prepared by contact with a solution of triethylsilane in heptane are thus more active than the reference catalyst. Catalysts D, E and F prepared by contact with a solution of triethylsilanol in heptane are similarly more active than the reference catalyst. Catalysts G, H and I prepared by contact with a solution of octamethylcyclotetrasiloxane in heptane are also more active than the reference catalyst.

In contrast, catalysts J and K prepared by contact with respectively a solution of dimethoxydimethylsiloxane (a non-cyclic siloxane) in heptane and a solution of hexamethyldisilane (a silane containing no Si—H bond) in heptane are less active than the reference catalyst.

These results are evidence that not all siliceous molecules enable the activity of the catalyst to be improved.

The selectivity for the formation of butene is defined on the basis of the contents of the various reaction products in the reaction medium, as follows:

$$\text{selectivity} = \frac{1But + cis2But + trans2But}{1But + cis2But + trans2But + nC4}$$

with 1 But, the content by mass of 1-butene,
cis2But, the content by mass of cis-2-butene,
trans2But, the content by mass of trans-2-butene
nC4, the content by mass of butane The selectivity increases with decline in the formation of butane.

The selectivity is evaluated for a conversion of 1,3-butadiene of 99% (the conversion is defined as the ratio of the quantity of 1,3-butadiene reacted to the starting quantity of 1,3-butadiene). The selectivities of the catalysts prepared according to the examples above are given in Table 2.

TABLE 2

Selectivities of the catalysts prepared according to the examples above

| Catalyst | Silicon compound used | Selectivity (%) |
|---|---|---|
| A (reference) | — | 85.5 |
| C | triethylsilane - 3 wt. % Si | 86 |
| E | triethylsilanol - 3 wt. % Si | 94 |
| H | octamethylcyclotetrasiloxane - 70° C. | 86 |
| I | octamethylcyclotetrasiloxane - 180° C. | 88 |

Catalysts C and H prepared by contact with respectively a solution of triethylsilane in heptane and a solution of octamethylcyclotetrasiloxane in heptane show a selectivity for the formation of butene very slightly greater than that of the reference catalyst, whereas they are much more active than the reference catalyst (cf. Table 1).

This selectivity is further improved with the catalyst I prepared by contact at 180° C. with a solution octamethylcyclotetrasiloxane in heptane, then with the catalyst E prepared by contact with a solution of triethylsilanol in heptane, the two catalysts I and E being similarly much more active than the reference catalyst (cf. Table 1).

The invention claimed is:

1. A process for preparing a selective hydrogenation catalyst comprising, contacting a catalyst precursor in the metallic form, in the liquid phase and in the presence of a reducing and/or inert atmosphere, with a non-polar solvent containing a silicon compound, that is a silane containing at least one Si—H bond and at least one Si—C bond, of the formula $Si_xH_yR_z$, wherein x is an integer of 1 to 6, y is an integer of 1 to 2x+1, and z is an integer of 1 to 2x+1, the sum of y+z being 2x+2, and R is a monovalent hydrocarbon radical, identical or different for each valence, that is a saturated aliphatic radical, an unsaturated aliphatic radical, a cycloalkyl radical, an aryl radical or an arylalkyl radical, a silanol of the formula $Si_x(OH)R_{2x+1}$, wherein x is an integer within the range 1 to 6 and R is a monovalent hydrocarbon radical, identical or different for each valence, that is a saturated aliphatic radical, an unsaturated aliphatic radical, a cycloalkyl radical, an aryl radical or an arylalkyl radical or a cyclic siloxane in which a principal —Si—O—Si—O— chain forms a ring and is composed of $(R_2SiO)_n$ units, with n being an integer of 3 to 11, and R is a monovalent hydrocarbon radical, identical or different for each valence, that is a saturated aliphatic radical, an unsaturated aliphatic radical, a cycloalkyl radical, an aryl radical or an arylalkyl radical, wherein the catalyst precursor, comprises palladium in the metallic form and at least one support comprising at least one simple oxide that is alumina, silica, titanium oxide, cerium oxide or zirconium dioxide.

2. A process according to claim 1, wherein the non-polar solvent is an aliphatic hydrocarbon solvent, a cyclic hydrocarbon solvent, an aromatic hydrocarbon solvent, a partially saturated gasoline, a partially hydrogenated effluent derived from a selective hydrogenation process, or a mixture of these solvents.

3. A process according to claim 1, wherein the silicon compound is present in the non-polar solvent in a concentration between 0.01 and 10 wt. % of silicon.

4. A process according to claim 1, wherein contacting is performed at a temperature within the range 20 to 200° C.

5. A process according to claim 1, which further comprises, before contacting:
    a) at least one impregnation of a solution containing at least one precursor of palladium is impregnated onto the support,
    b) at least once drying the impregnated support resulting from a),
    c) at least one calcining of dried support resulting from b), so as to obtain palladium in oxide form,
    d) at least one reductive treatment of calcined support resulting from c) by contact with a reducing gas so as to obtain palladium in the metallic form.

6. A process according to claim 5, wherein drying b) is performed at a temperature within the range 20 to 160° C., calcining c) is performed at a temperature within the range 150 to 800° C. and d) reductive treatment by contact with a reducing gas is performed at a temperature above or equal to 50° C.

7. A process according to claim 5 further comprising e), wherein a passivation of the catalyst precursor is performed by a sulphur compound, said passivation being performed either after calcination c) and before d) reductive treatment of the catalyst precursor, or after d) reductive treatment of the catalyst precursor, or after contact of precursor and solvent.

8. A catalyst obtained by the process according to claim 1.

9. A process of selective hydrogenation, wherein the catalyst in the metallic form and prepared according to claim 1 is placed in contact with a feed of polyunsaturated hydrocarbons containing at least 3 carbon atoms per molecule and having a final boiling point below or equal to 250° C.

10. A process according to claim 9, wherein the feed is a C3 steam-cracking cut, a C4 steam-cracking cut a C5 steam-cracking cut or a steam-cracking gasoline, in such a way as to obtain a partially hydrogenated effluent.

11. A process according to claim 10, wherein at least a part of the partially hydrogenated effluent is used as a non-polar solvent in process of preparation of the selective hydrogenation catalyst.

* * * * *